US009796921B2

United States Patent
Pecinovsky et al.

(10) Patent No.: US 9,796,921 B2
(45) Date of Patent: Oct. 24, 2017

(54) BORON COMPOUNDS FOR USE IN SCINTILLATORS AND ADMIXTURE TO SCINTILLATORS

(71) Applicant: Colorado School of Mines, Golden, CO (US)

(72) Inventors: Cory Pecinovsky, Longmont, CO (US); Pascale Meysing, Golden, CO (US); Adam Mahl, Denver, CO (US); John Dorgan, Golden, CO (US); Uwe Greife, Golden, CO (US); Tyler Remedes, Colorado Springsw, CO (US)

(73) Assignee: Colorado School of Mines, Golden, CO (US)

( * ) Notice: Subject to any disclaimer, the term of this patent is extended or adjusted under 35 U.S.C. 154(b) by 6 days.

(21) Appl. No.: 14/452,007

(22) Filed: Aug. 5, 2014

(65) Prior Publication Data

US 2016/0355729 A1 Dec. 8, 2016

Related U.S. Application Data

(60) Provisional application No. 61/862,334, filed on Aug. 5, 2013.

(51) Int. Cl.

| | | |
|---|---|---|
| *C09K 11/06* | (2006.01) | |
| *G01T 3/06* | (2006.01) | |
| *C07F 5/04* | (2006.01) | |
| *G21K 4/00* | (2006.01) | |
| *G01T 1/204* | (2006.01) | |

(52) U.S. Cl.
CPC ............... *C09K 11/06* (2013.01); *C07F 5/04* (2013.01); *G01T 1/2042* (2013.01); *G01T 3/06* (2013.01); *G21K 4/00* (2013.01)

(58) Field of Classification Search
CPC .......... G01T 1/1642; G01T 3/00; C09K 11/06
See application file for complete search history.

(56) References Cited

U.S. PATENT DOCUMENTS

| 2,880,326 | A  | * | 3/1959  | Musicant ..................... 250/392 |
| 7,067,079 | B2 |   | 6/2006  | Bross et al. |
| 2013/0270443 | A1 | * | 10/2013 | Dijkstra et al. ............... 250/366 |

OTHER PUBLICATIONS

Bao et al., "Water-Soluble Hyperbranched Polyelectrolytes with High Fluorescence Quantum Yield: Facile Synthesis and Selective Chemosensor for Hg2+ and Cu2+ Ions," Journal of Polymer Science Polymer Chemistry, 2010, vol. 48(15), pp. 3431-3439, 2 page, abstract only.
Bell et al., "Boron-loaded silicone rubber scintillators," IEEE Transactions on Nuclear Science, 2004, vol. 51(4), pp. 1773-1776, 1 page, abstract only.
Bell et al., "Organic scintillators for neutron detection," SPIE, 2003, 1 page, abstract only.
Drake et al., "New electronically black neutron detectors," Nuclear Instruments and Methods in Physics Research Section A: Accelerators, Spectrometers, Detectors and Associated Equipment, 1986, vol. A247(3), pp. 576-582 (1986), 1 page, abstract only.

(Continued)

*Primary Examiner* — David Porta
*Assistant Examiner* — Hugh H Maupin
(74) *Attorney, Agent, or Firm* — Sheridan Ross P.C.

(57) ABSTRACT

The present disclosure is directed to liquid boron compounds for use in scintillation. The present disclosure further relates to liquid boron compounds for admixture to plastic and liquid scintillators.

17 Claims, 18 Drawing Sheets

(56) References Cited

OTHER PUBLICATIONS

Drake et al., "New electronically black neutron detectors," Los Alamos National Laboratory, LA-10611, 1986, retrieved from http://www.iaea.org/inis/collection/NCLCollectionStore/_Public/17/078/17078930.pdf, retrieved on Apr. 22, 2016, 17 pages.

U.S. Appl. No. 14/973,318, filed Dec. 17, 2015, Sellinger et al.

Geny et al., "Cobalt(I)-mediated preparation of polyborylated cyclohexadienes: Scopte, limitations, and mechanistic insight," Chemistry a European Journal, 2007, vol. 13(19), pp. 5408-5425, 2 page, abstract only.

Iannazzo et al., "Alkynylboronates and -boramides in CoI- and RhI-Catalyzed [2+2+2] Cycloadditions: Construction of Oligoaryls through Selective Suzuki Couplings," European Journal of Organic Chemistry, 2011, vol. 2011(18), pp. 3283-3292, 2 page, abstract only.

Liu et al., "Synthesis and properties of starburst amorphous molecules: 1,3,5-tris(1,8-naphthalimide-4-yl)benzenes," Synthetic Metals, 2010, vol. 160(19-20), pp. 2055-2060, 1 page, abstract only.

Matsumoto et al., "A kinetically protected pyrene: molecular design, bright blue emission in the crystalline state and aromaticity relocation in its dicationic species," Chemical Communications, 2014, vol. 50(75), pp. 10956-10958, 2 pages, abstract only.

Meijer et al., "Towards Compact Antineutrino Detectors for Safeguarding Nuclear Reactors," IAEA Report, IAEA-CN-184/74, 2010, 6 pages.

Pla-Dalmau et al., "Low-cost extruded plastic scintillator," Nuclear Instruments and Methods in Physics Research Section A: Accelerators, Spectrometers, Detectors and Associated Equipment, 2001, vol. 466(3), pp. 482-491.

Seven et al., "M. High-Yield Syntheses and Reactivity Studies of 1,2-Diborylated and 1,2,4,5-Tetraborylated Benzenes," Organometallics, 2014, vol. 33(5), pp. 1291-1299, 1 page, abstract only.

\* cited by examiner

Chemical Formula: C₉H₁₁BO₃
Exact Mass: 178.08
Molecular Weight: 177.99
m/z: 178.08 (100.0%), 177.08 (24.8%), 179.08 (9.8%), 178.09 (2.5%)
Elemental Analysis: C, 60.73; H, 6.23; B, 6.07; O, 26.97

Chemical Formula: C₁₀H₁₃BO₃
Exact Mass: 192.10
Molecular Weight: 192.02
m/z: 192.10 (100.0%), 191.10 (24.2%), 193.10 (10.9%), 194.10 (1.1%)
Elemental Analysis: C, 62.55; H, 6.82; B, 5.63; O, 25.00

Chemical Formula: C₂₁H₂₁BO₃
Exact Mass: 332.16
Molecular Weight: 332.20
m/z: 332.16 (100.0%), 331.16 (24.8%), 333.16 (23.1%), 332.17 (5.7%), 334.17 (2.6%)
Elemental Analysis: C, 75.93; H, 6.37; B, 3.25; O, 14.45

BORON COMPOUNDS FOR USE IN SCINTILLATORS AND ADMIXTURE TO SCINTILLATORS

CROSS REFERENCE TO RELATED APPLICATIONS

This application claims the benefit of U.S. Provisional Patent Application No. 61/862,334 entitled "Boron Compounds For Use In Scintillators And Admixture To Scintillators" filed on Aug. 5, 2013, the entire disclosure of which is incorporated by reference herein.

FIELD

The disclosure relates generally to scintillators and more particularly to boron compounds for use in scintillators and admixture to scintillators.

BACKGROUND

Nuclear proliferation represents a global and imminent threat to the safety and security of the international community. Smuggling of contraband radioactive materials can be counteracted with effective neutron detection technologies deployed along shipping routes and at potential terrorist target locations. However, established technologies commonly utilize helium-3, which is a rare isotope of which in recent years demand has overtaken supply. Thus, the production of effective, inexpensive, and widely deployable neutron detectors is a high priority. Liquid and/or plastic scintillating detectors are a promising prospect for inexpensive neutron detectors.

A scintillator is a material that exhibits scintillation (e.g., the property of luminescence) when excited by ionizing radiation. Sometimes, the excited state is metastable, so the relaxation back out of the excited state is delayed (necessitating anywhere from a few microseconds to hours depending on the material): the process then corresponds to either one of two phenomena, depending on the type of transition and hence the wavelength of the emitted optical photon: delayed fluorescence or phosphorescence, also called afterglow.

Atomic and subatomic particles are detected by the signature they produce through interaction with their surroundings. The interactions result from the particles' fundamental characteristics. Neutron detection may be achieved by elastic scattering reactions (also referred to as proton-recoil), where high energy neutrons may be detected indirectly through elastic scattering reactions. In particular, in response to radiation, as a neutron is not charged it does not interact via the Coulomb force (e.g., electrostatic interactions between electrically charged particles) and therefore does not interact with the electrons in a scintillation material, but when neutrons collide with the nucleus of atoms in a detector, the collision transfers energy to that nucleus and creates an ion (e.g., ionization), which is detectable. Kinematically, a neutron can transfer more energy to light nuclei such as hydrogen or helium than to heavier nuclei. Detectors relying on elastic scattering are called fast neutron detectors. Recoiling nuclei can ionize and excite further atoms through collisions. Charge and/or scintillation light produced in this way can be collected to produce a detected signal.

Thus, fast neutrons (e.g., generally >0.5 MeV) primarily rely on the recoil proton in a (n,p) scattering reaction and materials rich in hydrogen (e.g. liquid and plastic scintillators) are therefore well-suited for their detection. Slow neutrons rely on nuclear reactions such as the (n,γ) or (n,α) reactions, to produce ionization. Their mean free path is therefore quite large unless the scintillator material contains nuclides having a high cross section for these nuclear reactions, such as $^6$Li or $^{10}$B. Materials such as LiI(Eu) or glass silicates are therefore well-suited for the detection of slow (thermal) neutrons.

Fast neutron as well as thermalized neutron detection is a difficult undertaking but necessary in basic nuclear science as well as in the applied fields of nuclear energy, nuclear safeguards, nuclear forensics and homeland security. Neutrons interact differently with commonly used detector materials compared to, for example, gamma radiation, which is usually also prevalent in neutron radiation fields. Therefore, efficient neutron detection usually requires large detectors which need to employ a mechanism to distinguish the neutron and gamma radiation.

The term "liquid scintillator" typically refers to a liquid solution of one or more organic scintillators in a solvent. The term "plastic scintillator" typically refers to a scintillating material in which the primary fluorescent emitter, called a fluor, is suspended in the base, a solid polymer matrix.

Scintillators may be used as neutron (e.g., radiation) detectors, in neutron and high energy particle physics experiments, in new energy resource exploration, in nuclear cameras, for computed tomography, and for gas exploration, among other uses. In particular, a scintillator may be used in conjunction with a photomultiplier tube ("PMT").

PMTs absorb the light emitted by the scintillator and reemit it in the form of electrons via the photoelectric effect. The subsequent multiplication of those electrons (sometimes called photo-electrons) results in an electrical pulse which can then be analyzed and yield meaningful information about the particle that originally struck the scintillator. Photomultiplier tubes (e.g., vacuum tubes or vacuum phototubes) are extremely sensitive detectors of light in the ultraviolet, visible, and near-infrared ranges of the electromagnetic spectrum. Thus, scintillators in combination with a PMT are useful in survey meters used for detecting and measuring radioactive contamination and monitoring nuclear material. However, detection in scintillators is based on the collection of luminescence emitted by the scintillator components when they interact with particles of nuclear origins. Therefore, to maximize light collection, scintillator transparency is desired.

In addition, natural boron or $^{10}$B loaded scintillators are costly. Therefore, scintillators that may be produced at lower cost, including any that may be produced using different compounds to reduce cost and improve ease of manufacture, are desired.

SUMMARY

These and other needs are addressed by the various embodiments and configurations of the present disclosure.

The following presents a simplified summary of the disclosure to provide an understanding of some aspects of the disclosure. This summary is not an extensive overview of the disclosure and its various embodiments. It is intended neither to identify key or critical elements of the disclosure nor to delineate the scope of the disclosure but to present selected concepts of the disclosure in a simplified form as an introduction to the more detailed description presented below.

In some aspects, various methods to accomplish neutron detection include introducing into the detector material atoms or compounds containing an isotope with which neutrons undergo a nuclear reaction with a high probability. It is thereby possible to produce a unique signature detecting the neutron radiation field. Typically, such techniques may be used in liquid or plastic scintillators into which $^6$Li, $^{10}$B, or gadolinium containing compounds are dissolved.

However, the boron containing compounds used so far have been either flammable or very expensive and only of limited availability in their $^{10}$B enriched form. The present disclosure is directed to transparent boron compounds that are neither flammable nor combustible and can be easily produced from commercially available enriched $^{10}$boron acid.

In various aspects, the present disclosure is directed to natural and $^{10}$B-enriched liquid boron compounds that are synthesized to be admixed to plastic and liquid scintillators in neutron radiation detection. The boron containing compounds used prior to this disclosure have been either flammable or very expensive and only of limited availability in their $^{10}$B enriched form. In contrast, the present disclosure is directed to transparent boron compounds that are neither flammable nor combustible and can be easily produced from commercially available enriched $^{10}$boron acid. The compounds can be admixed to standard recipes for extruded and cast polystyrene based plastic scintillators, as well as to commercially available liquid scintillator mixtures. Neutron sensitivity via neutron capture on $^{10}$B is obtained, and neutron-gamma pulse shape discrimination (PSD) may be retained in scintillators that exhibited it prior to the admixture.

In further aspects, the compounds synthesized may be selected to be neither flammable nor combustible, and may thereby enable widespread use in large detectors. Further, the compounds may be admixed to plastic and/or liquid scintillators (e.g., admixed to standard recipes for extruded and cast polystyrene based plastic scintillators, as well as admixed to commercially available liquid scintillator mixtures).

In embodiments, scintillators of the present disclosure include a plastic matrix, one or more fluorescent dopants, and a boron compound that is soluble in the plastic. In further embodiments, methods to functionalize boron compounds to enhance solubility in specific plastics are disclosed. In addition, methods of producing a boron compound that shows improved solubility in polystyrene and other plastics, and/or improved transparency, and/or that acts as a fluorescent dopant, are disclosed. Further, methods that use inexpensive plastic matrices, boron-containing compounds, and fluorescent dopants combined with continuous extrusion processing are disclosed.

In addition, to prevent phase separation of the polymer base and the boron-containing compound, high solubility is paramount. Therefore, in other aspects, this disclosure provides methods to produce plastic-soluble borates.

Further, as discussed herein, it is advantageous to reduce the generation of luminescence from interactions of the detector with gamma rays. Therefore, in additional aspects, this disclosure provides scintillators containing elements with low atomic numbers to decrease gamma ray sensitivity. In embodiments, elements with low atomic numbers may be the only elements included in the scintillator.

Still further, the present disclosure is directed generally to devices that include a scintillator that is coupled to an electronic light sensor. In embodiments, the electronic light sensor may be a photomultiplier tube or a photodiode, and the device may be a scintillation detector or scintillation counter.

In addition, the present disclosure is directed to methods to produce a material which can serve as an efficient plastic scintillator for neutron detection. Such a plastic scintillator may advantageously provide for discrimination against gamma rays and other forms of radiation. More specifically, the scintillators of the present disclosure may include boron. Plastic scintillators that include boron may advantageously enable or improve generation of a clear signal for neutrons against gamma rays. These and other advantages will be apparent from the disclosure contained herein.

In addition, the present disclosure is directed to methods to produce a material which can serve as an efficient plastic scintillator for neutron detection. Such a plastic scintillator may advantageously provide for discrimination against gamma rays and other forms of radiation. More specifically, the scintillators of the present disclosure may include boron. Plastic scintillators that include boron may advantageously enable or improve generation of a clear signal for neutrons against gamma rays.

In certain aspects, this disclosure solves the problem of producing effective low cost liquid or plastic scintillators; for example, boron-loaded scintillators are obtained. In addition, in other aspects, this disclosure solves the problems of improved transparency and light yield from liquid or plastic scintillators. For example, incorporation of fluorescent dopants in the liquid or the plastic matrix enhances the scintillation performance. In embodiments, the boron esters disclosed herein can act as scintillators when fluorescent dopants are admixed. Fluorescence dopants can make fluorescence light production more efficient. They can also shift the light emission of the plastic matrix to longer wavelengths where common photodetectors are most sensitive. Moreover, when used in high concentrations, they improve the neutron/gamma ray discrimination capabilities of the scintillator.

In some aspects, this disclosure enables the choice and production of borate esters for enhancing solubility of boron in liquid and/or plastic matrices, which renders possible the incorporation of boron in plastic without decreasing light yield appreciably. In further aspects, this disclosure synthesizes natural and $^{10}$B-enriched liquid boron compounds to be used as non-flammable base materials for liquid scintillators in neutron radiation detection. Also, incorporation of boron may be important for being able to discriminate neutrons from gamma rays during interrogation of cargo shipments.

In additional aspects, this disclosure enables efficient neutron detection to distinguish the neutron and gamma radiation by introducing into the detector boron compounds with functional groups to produce scintillation that directly constitute a non-flammable liquid scintillator, which is neutron sensitive via neutron-proton scattering (e.g., shows pulse shape discrimination), and neutron capture on $^{10}$B.

Products of this disclosure may be materials that are highly transparent boron-loaded scintillator for neutron detection. The scintillator material can be produced continuously by processes including, but not limited to, extrusion to produce profile shapes in long strips that can be combined to create large detectors. Large detectors can be used in applications such as neutron detector portals at border crossings for homeland security. Other potential sectors of application include, for example, safety equipment, measurement instrumentation, nuclear medicine, nuclear energy production, and various particle accelerators.

Advantages over existing technologies include a higher transparency enabling production of large detectors, low production cost and the use of low-cost, high throughput techniques such as extrusion for production. In addition, the exemplary methods disclosed herein may advantageously enable production on a large scale at a low cost. Further, the present disclosure provides boron-loaded scintillators with high neutron detection efficiency and superior light collection. These and other advantages will be apparent from the disclosure contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The above-described embodiments and configurations are neither complete nor exhaustive. As will be appreciated, other embodiments of the disclosure are possible utilizing, alone or in combination, one or more of the features set forth above or described in detail below.

DETAILED DESCRIPTION

Figure 1:
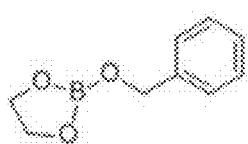
FIG. 1 shows illustrative natural boron containing compounds in accordance with various embodiments of the present disclosure.
Figure 1:
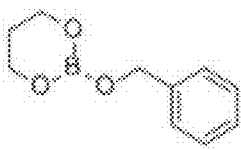
Figure 1:
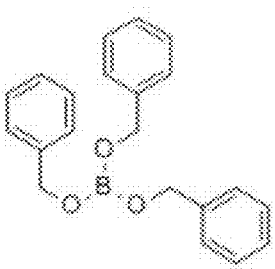

The present disclosure relates to methods of producing boron compounds for use in scintillators and as admixtures to scintillators. More specifically, the present disclosure relates to methods of producing boron compounds for use as transparent admixtures to commercially available or widely used liquid and plastic scintillator formulations. Such scintillators can be used to detect neutron radiation through the formation of a light signal upon interaction with neutrons, for example. Thus, in embodiments, the boron esters disclosed herein by themselves can act as scintillators when fluorescent dopants are admixed.

In embodiments, scintillators of the present disclosure include liquid scintillators having a boron compound, as well as scintillators having a plastic matrix, one or more fluorescent dopants, and a boron compound that is soluble in the plastic. In further embodiments, methods to functionalize boron compounds to enhance solubility in specific plastics are disclosed. In addition, methods of producing a boron compound that shows improved solubility in polystyrene and other plastics, and/or improved transparency, and/or that acts as a fluorescent dopant, are disclosed. Further, methods that use inexpensive plastic matrices, boron-containing compounds, and fluorescent dopants combined with continuous extrusion processing are disclosed.

As discussed above, efficient neutron detection usually requires large detectors which need to employ a mechanism to distinguish the neutron and gamma radiation. Exemplary methods to accomplish this introduce into the detector material atoms or compounds containing an isotope with which neutrons undergo a nuclear reaction with a high probability. It is thereby possible to produce a unique signature detecting the neutron radiation field. This technique may be used in liquid or plastic scintillators into which $^6$Li, $^{10}$B, or gadolinium containing compounds are dissolved.

Various embodiments of the present disclosure relate to transparent boron compounds, including compounds that are neither flammable nor combustible and can be easily produced from commercially available enriched $^{10}$boricacid. The compounds include compounds that have been admixed to standard recipes for extruded and cast polystyrene based plastic scintillators, as well as to commercially available liquid scintillator mixtures. In addition, in various embodiments of the compounds disclosed herein, neutron sensitivity via neutron capture on $^{10}$B is exhibited, and neutron-gamma PSD is retained in scintillators that exhibited it prior to the admixture.

In neutron detection, incoming fast neutrons lose energy through elastic collisions with (predominantly) the hydrogen nuclei (protons) in the scintillator. This interaction produces a first signal in a scintillator. In some types of scintillators, a pulse shape of the photon pulse can provide information on the incident radiation type (e.g., neutron-gamma discrimination). After the neutrons have been slowed down (e.g., following several collisions) they can undergo nuclear reactions with a neutron sensitive dopant, represented by the following equations:

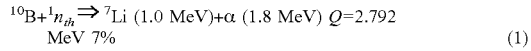

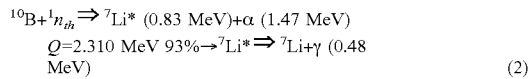

However, due to the fact that natural boron or $^{10}$B loaded scintillators are commercially available but very expensive, it is advantageous to have alternatives for such scintillators. Such alternatives would make use of new and/or easier to produce compounds, which could be admixed (e.g., loaded in) to commonly used scintillator materials. Thus, in embodiments disclosed herein, liquid compounds containing boron display scintillation properties and may be used as transparent admixtures to commercially available or widely used liquid and plastic scintillator formulations. Various embodiments disclosed herein use several liquid, boron containing, compounds that by themselves exhibit scintillating properties.

Also, similar to other scintillators, the scintillation performance of these compounds may be enhanced by the admixture of fluorescent dopants at the few percent level. Fluorescent dopants not only provide more efficient fluorescence light production but also shift the light emission to wavelengths where common photo-detectors are most sensitive.

Boron containing compounds, including synthesized boron containing compounds, of the present disclosure are borate esters. The material may use natural boron 10B-enriched material produced starting with commercially easily available boric acid or $^{10}$B-acid. The borate ester may include natural boron, boron-10 enriched boron, or some combination of boron and/or isotopically enriched borons. The borate ester can contain a single boron atom per molecule or have a repetitive cyclic or polymeric structure. The borate ester can be functionalized to increase solubility in the plastic matrix. The borate ester can contain phenyl rings or other chemical groups to enhance scintillation performance by acting as a primary, secondary, or tertiary fluor.

For example, natural boron may be used. Also, commercially available boric acid or $^{10}$B-acid may be used to produce $^{10}$B-enriched material. A synthesis of borate esters can be performed with a Dean-Stark apparatus, as described herein. In various embodiments, a boron compound (e.g., boric acid, boron oxide, boronic acids, borinic acids, and phenylboronic acids, among others) may be combined with a functional group (e.g., benzyl alcohol, propylene glycol, ethylene glycol, ethanol, and methanol, propanol, butanol, phenol, pyrocatechol, among others) to provide a neutron sensitive scintillator base which is advantageously nonflammable. In contrast, some neutron sensitive scintillator bases are problematic. For example, methanol has been used as an additive to other scintillators in the form trimethyl borate, but is problematic because it has a low boiling point and is flammable. Embodiments of the present disclosure are advantageous over trimethylborate due to lower flammability. Thus, in various embodiments, trimethylborate is excluded as a scintillator in the present disclosure.

The synthesis of borate esters can be performed with a Dean-Stark apparatus by reacting one equivalent of boric acid with 3 equivalents alcohol, according to the reaction shown in the following equation:

In Equation 3, the R-group represents a chemical functional group and may be chosen to enhance scintillation efficiency or other parameters, such as solubility of the borate ester in the polymer host, which might be relevant for a specific application. Examples include, but are not limited to, ethanol, methanol, propanol, butanol, benzyl alcohol, phenol, pyrocatechol, ethylene glycol, and propylene glycol. The R-group can also serve as a fluorescent moiety that improves the scintillation performance.

Synthesized borate ester can include trimethyl borate, which may be used in scintillator applications; however, trimethyl borate is problematic due to its low flash point of −6° Celsius. Thus, in various embodiments, trimethylborate is excluded in the synthesized compounds of the present disclosure. Additionally, synthesized borate esters may include any combination of a boron compound (e.g., boric acid, boron oxide, boronic acids, borinic acids, and phenylboronic acids) with a functional group (e.g., benzyl alcohol, propylene glycol, ethylene glycol, ethanol, methanol, propanol, butanol, phenol, and pyrocatechol) to provide a neutron sensitive scintillator compound which is non-flammable. The functional group(s) may be chosen based on various properties. In addition, to enhance scintillation efficiency, standard fluorescent dopants may be added (e.g., 2,5-diphenyloxazole (PPO), 9,10-diphenylanthracene (DPA), 1,4-bis(5-phenyloxazol-2-yl)benzene (POPOP), and fluorene).

Suitable fluorescent dopants may include 2,5 diphenyloxazole, 1,4,4-tetraphenyl-1,3-butadiene, p-terphenyl, p-quaterphenyl, anthracene, 1,4-diphenyl-1,3-butadiene, naphthalene, stilbene, biphenyl, 1,6-diphenyl-1,3,5-hexatriene, diphenylacetylene, diphenyldiacetylene, 2,4-bis(5-phenyloxazole-2-yl)benzene, 9,10-diphenylanthracene, 1,3-diphenyl-2-pyrazoline, diphenylethane, and 1-phenyl-1,3,3-trimethylindan, for example.

Various methods may be used to combine the plastics, borate esters, and dopants. Exemplary methods may include, but are not limited to, extrusion, injection molding, bulk polymerization, polymerization in a solvent, compression molding, blow molding, and fiber spinning. Plastic matrices may include, but are not limited to, polystyrene, polycarbonate, polyvinyltoluene, polymethylmethacrylate, and silicone rubbers, among others. The plastic raw material can be monomeric or a preformed polymer. The preformed polymer may be powder, pellets, other solid forms, in the rubbery state, or in liquid form. In embodiments, plastics containing only low atomic number elements may be used.

Thermodynamic calculations based on solubility parameters can be used to choose any suitable alcohols, phenols, glycols, or pyrocathecols to improve solubility of the borate ester. Solubility parameters can be computed by group contribution methods, which are techniques to estimate and predict thermodynamic and other properties from molecular structures. Exemplary group contribution methods include Fedor's or Hansen's methods. Other boron compounds containing one or several B—O bonds can also be used, including but not limited to, boron oxide, boronic acids, and borinic acids.

EXAMPLES

The following natural boron containing compounds as displayed in FIG. 1 were synthesized and used in various exemplary embodiments. The compounds shown in FIG. 1 are not classified as flammable or combustible. The compound shown at the top of FIG. 1 is the ester of ethylene glycol. The compound shown at the middle of FIG. 1 is the ester of propylene glycol. The compound shown at the bottom of FIG. 1 is tribenzyl borate. Tribenzyl borate has also been synthesized as the $^{10}$B enriched compound (also referred to as $^{10}$B enriched tribenzyl borate). All three compounds were confirmed as scintillators using a Horiba fluorescence spectrometer, as shown in FIG. 2.

Figure 2:
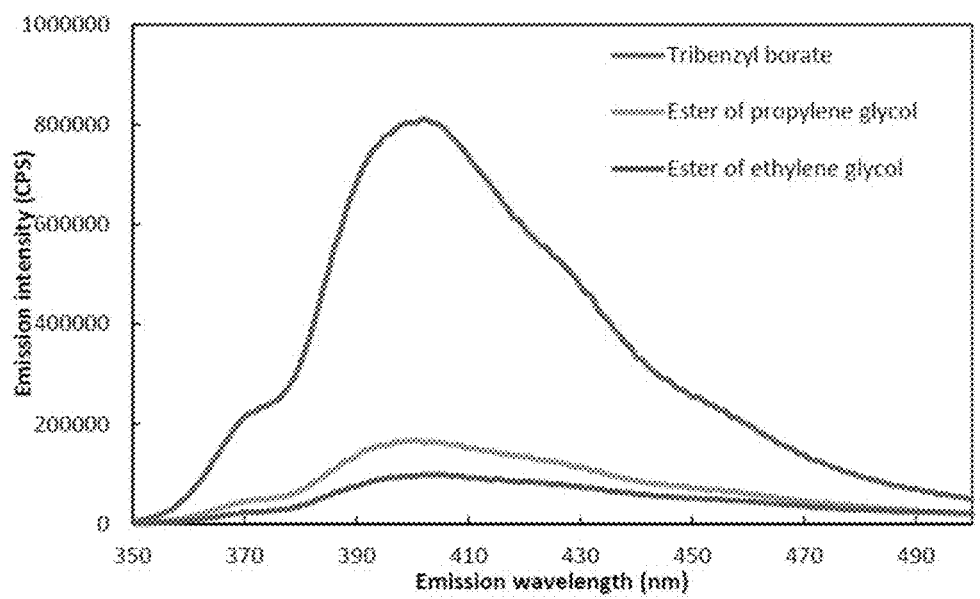
FIG. 2 shows illustrative fluorescence spectra of the compounds of FIG. 1 in accordance with various embodiments of the present disclosure.

FIG. 2 shows fluorescence spectra of the three boron containing liquids without PPO/POPOP addition, and normalized to relative maxima. The spectra were obtained with a Horiba Nanolog. The compounds synthesized were transparent, and solubility of the compounds was tested in standard plastic and liquid scintillators. In the tests, up to 20% solubility in the plastic matrices (e.g., extruded or cast polystyrene) was achieved, and up to 50% solubility in commercial liquid scintillators (e.g., EJ-301, produced by Eljen Technology) was achieved.

Such exemplary methods disclosed herein are transferable to other liquid scintillators as well as to other plastic solid matrices. Standard primary and secondary fluorescent dopants like fluorene, PPO, POPOP, and p-bis-(o-methylstyryl)-benzene (MSB) may be used for scintillation enhancement and wavelength shifting. Other fluorescent dopants may also be used.

Illustrative examples discussed herein show, e.g., transparent boron containing admixtures that may be used in cast plastic scintillators, extruded plastic scintillators, and liquid scintillators. In the following examples, neutron sensitivity was shown by detecting the thermal neutron capture on $^{10}$B.

Example 1

Figure 3:
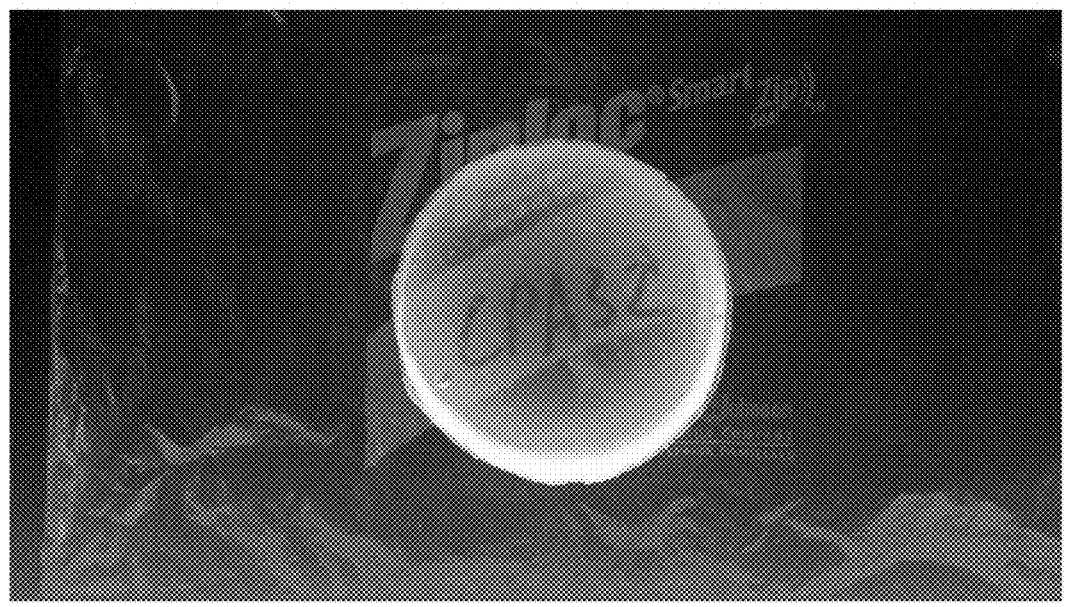
FIG. 3 shows an illustrative scintillator in accordance with various embodiments of the present disclosure.

In Example 1, a cast polystyrene containing 20% of the boric ester of propylene glycol, 1% PPO, and 0.3% POPOP was formed. FIG. 3 shows the transparency of the boron containing cast scintillator sample under UV-light. The sample is approximately 3 inches thick with a 2.5 inch diameter.

Figure 4:
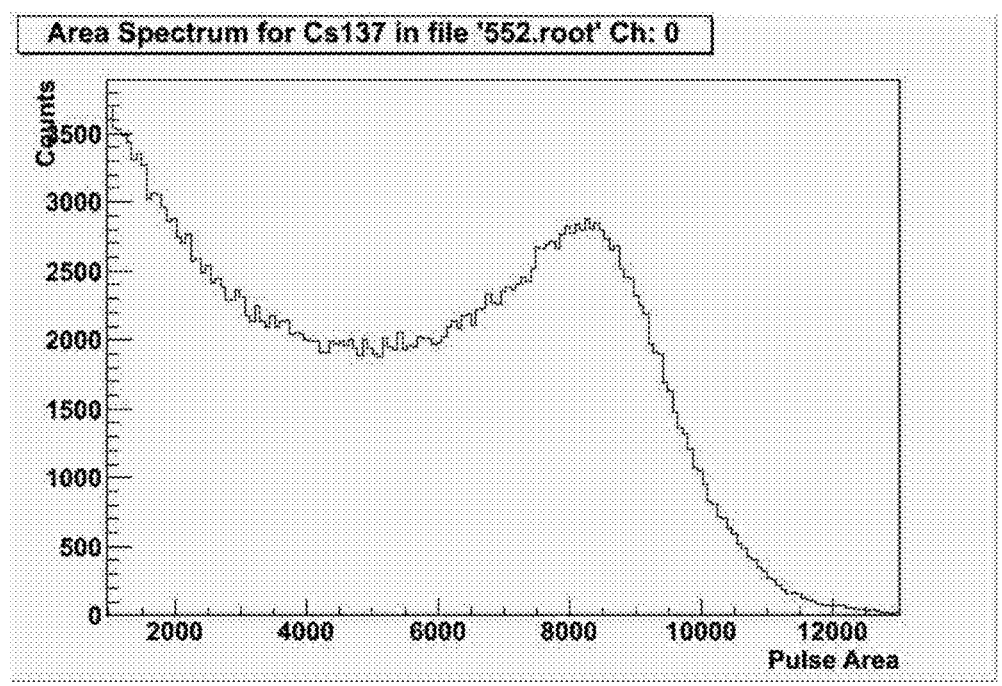
FIG. 4 shows an illustrative a 137Cs test in accordance with various embodiments of the present disclosure.

A 137-Cs source (e.g., 667 keV) was used to test for the response to gamma excitation. FIG. 4 shows the Compton edge of the detector response. For example, FIG. 4 shows a 137-Cs test showing Compton Edge from 667 keV gamma ray in the cast boron containing plastic scintillator sample of Example 1.

Figure 5:
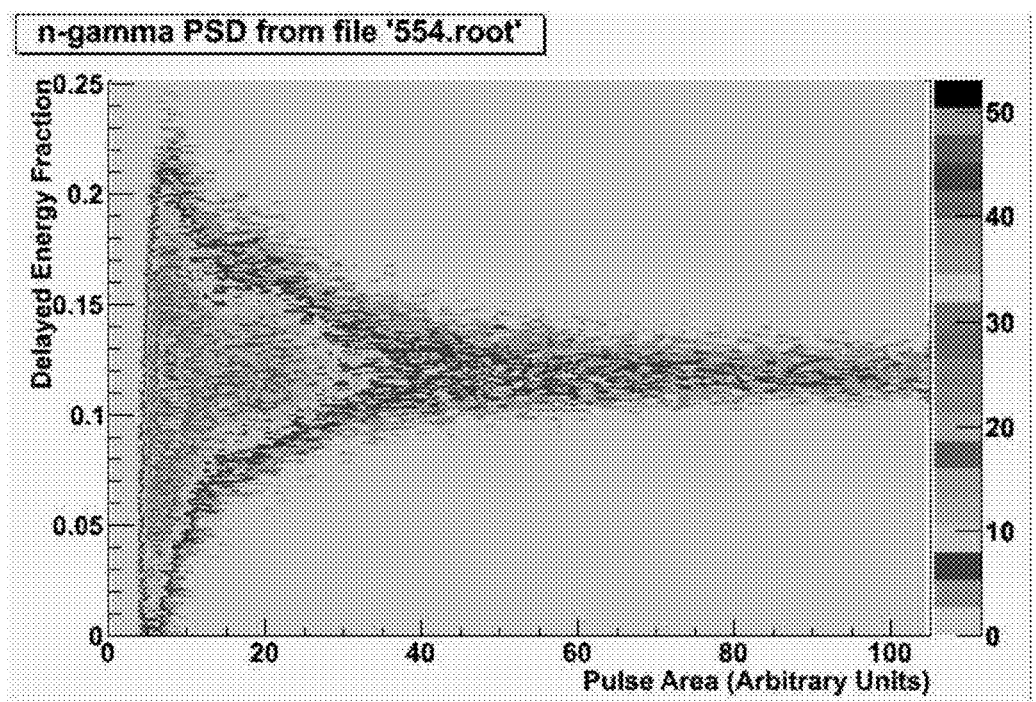
FIG. 5 shows an illustrative spectrum in accordance with various embodiments of the present disclosure.

Neutron sensitivity was tested using a 244Cm/13C fast neutron source in two configurations. Initially, lead shielding was used to reduce gamma radiation at the scintillator location and let the fast neutron spectrum pass nearly uninhibited. FIG. 5 shows the resulting spectrum (delayed area versus full pulse area), which does not exhibit neutron-gamma pulse shape discrimination (PSD); however, an indication for thermal neutron capture is already visible. For example, FIG. 5 shows a lead shielded 244-Cm/13-C source spectrum of the cast boron containing sample with thermal neutron capture at approximately Channel 20 on the x-axis. The colour scheme on the right of FIG. 5 and in the following figures indicates the number of events per 2-D spectrum bin.

To test where to expect the thermal neutron capture signal on $^{10}$B, which may lead to fast alpha particles in the exit channel, the response to energetic alpha particles was tested by placing a 241Am source onto the surface of the scintillator on the side of the scintillator opposite the photomultiplier.

Figure 6:
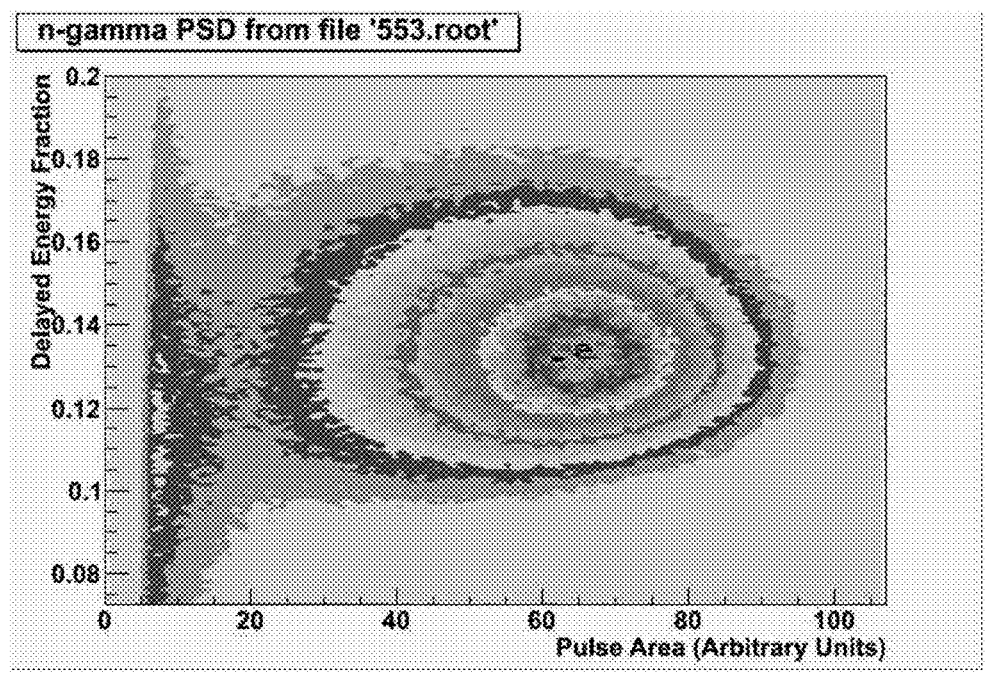
FIG. 6 shows an illustrative 241Am α signal in accordance with various embodiments of the present disclosure.

FIG. 6 shows a 241Am α signal in the cast boron containing scintillator sample. As shown in FIG. 6, the energetic alpha particles leave a clear signal in our cast boron containing sample.

Figure 7:
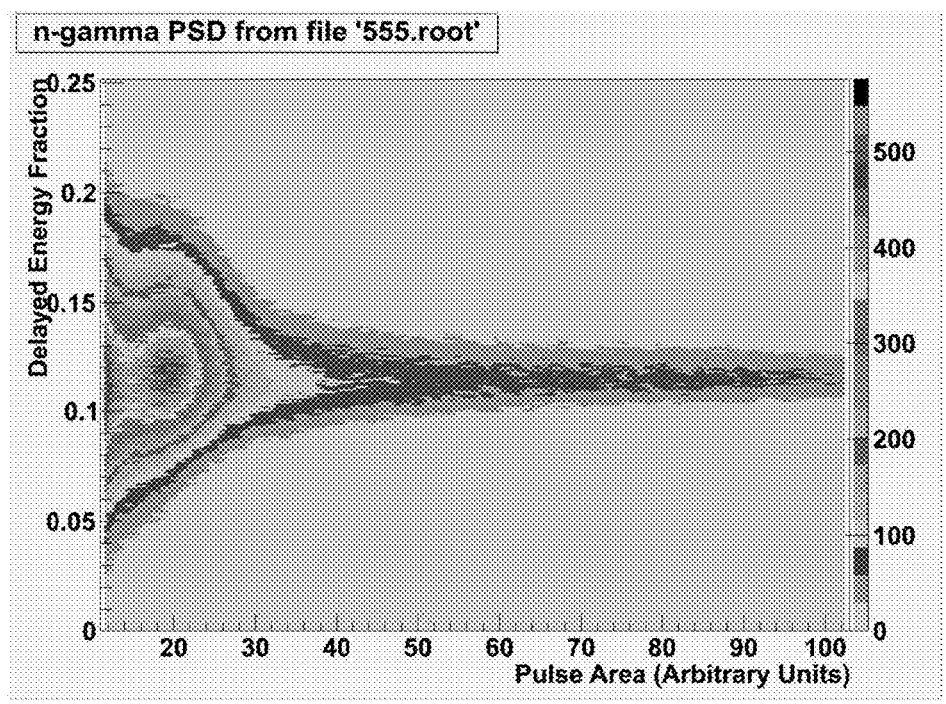
FIG. 7 shows an illustrative 244-Cm/13-C low energy spectrum in accordance with various embodiments of the present disclosure.

To enhance the thermal neutron flux, a plastic, hydrogen rich shielding was placed around the scintillator sample. A significant increase in the thermal neutron capture signal on $^{10}$B at the expected location in the low energy spectrum was observed, as shown in FIG. 7. For example, FIG. 7 shows a 244-Cm/13-C low energy spectrum for the cast boron containing sample showing electronic noise (e.g., PMT, which was also visible when the scintillator was removed), as well as a clearly separated peak for thermal neutron capture on $^{10}$B.

Example 2

Figure 8:
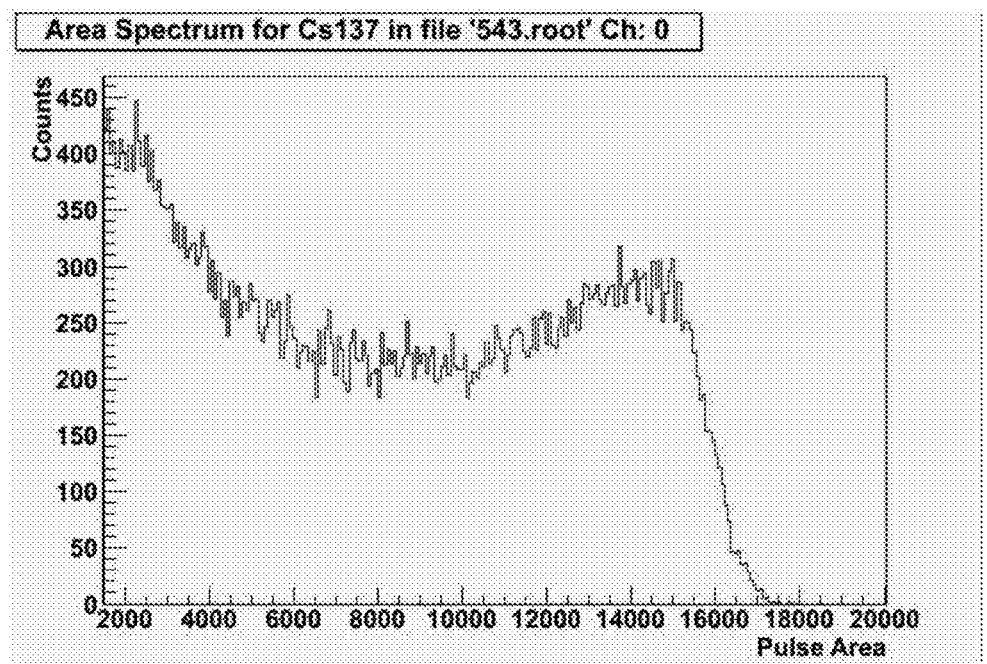
FIG. 8 shows an illustrative a 137Cs test in accordance with various embodiments of the present disclosure.
Figure 9:
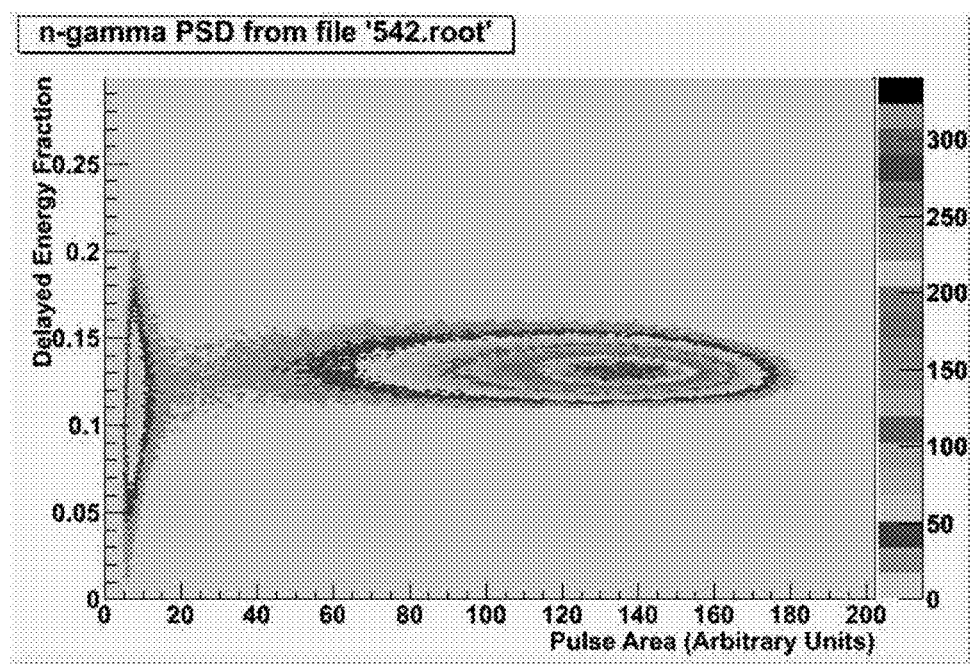
FIG. 9 shows an illustrative 241Am α signal in accordance with various embodiments of the present disclosure.
Figure 10:
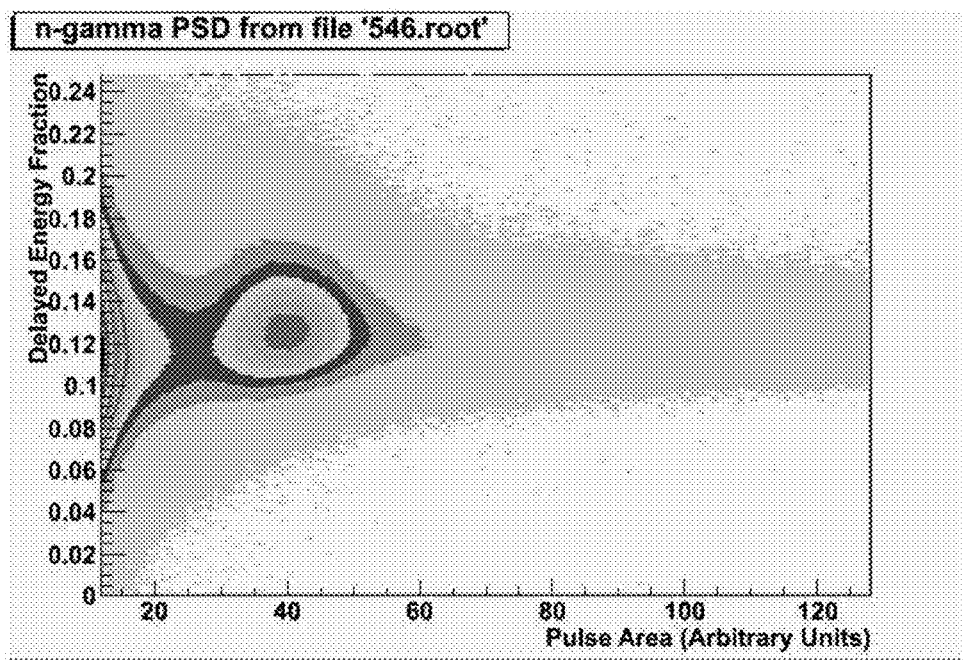
FIG. 10 shows an illustrative thermalized neutron capture from a 244-Cm/13-C source in accordance with various embodiments of the present disclosure.

Example 2 uses the same test conditions as Example 1. Example 2 is an extruded polystyrene containing 20% of boric ester of propylene glycol, 1% PPO, and 0.3% POPOP. FIG. 8 shows a 137Cs test showing Compton Edge from 667 keV gamma ray in the extruded boron containing plastic scintillator sample. FIG. 9 shows a 241Am α signal in the extruded boron containing scintillator sample. FIG. 10 shows thermalized neutron capture on $^{10}$B at approximately Channel 40 on the x-axis from a 244-Cm/13-C source in the extruded boron containing scintillator sample. The tests used the same testing setups that were used in Example 1.

Example 3

Figure 11:
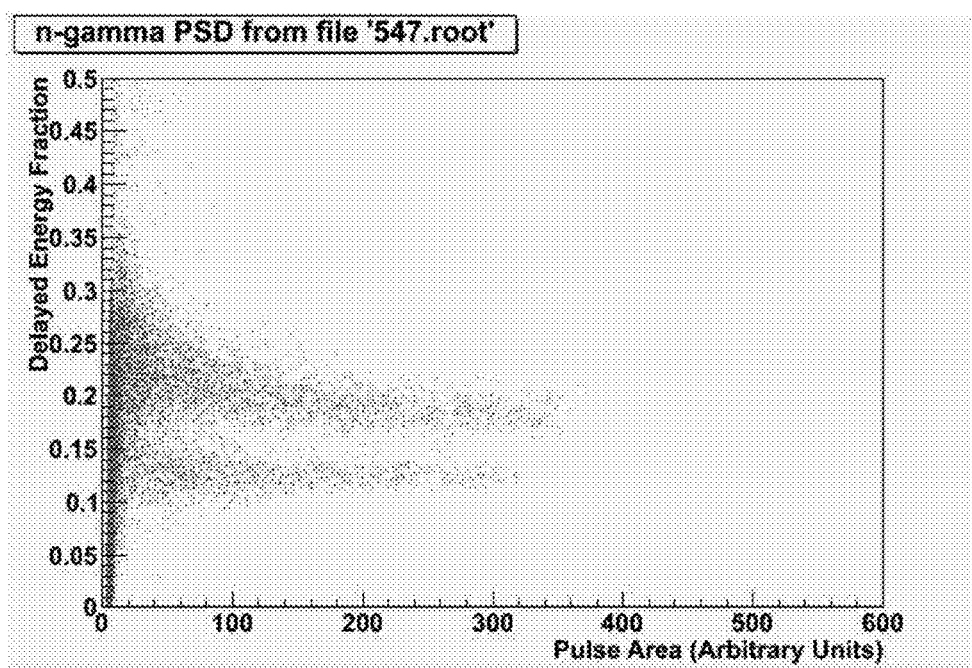
FIG. 11 shows an illustrative fast neutron spectrum from a 244-Cm/13-C source in accordance with various embodiments of the present disclosure.
Figure 12:
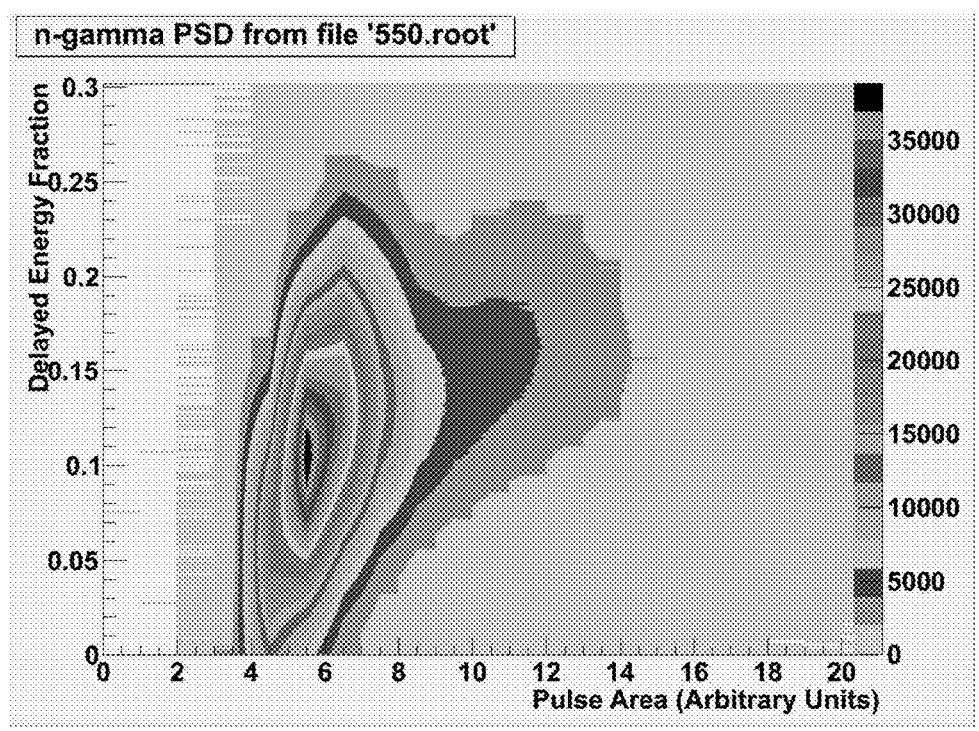
FIG. 12 shows an illustrative 244-Cm/13-C low energy spectrum in accordance with various embodiments of the present disclosure.

Example 3 uses the same test conditions as Examples 1 and 2. Example 3 is a liquid scintillator mixture containing 50% of tribenzyl borate and 50% of commercially available EJ-301 liquid scintillator. FIG. 11 shows a fast neutron spectrum from the 244-Cm/13-C source showing that the liquid scintillator mixture has retained the original pulse shape discrimination of the EJ-301 and the tribenzyl borate. FIG. 12 shows a low energy spectrum showing thermalized neutron capture on $^{10}$B for the boron containing liquid scintillator mixture. In embodiments, this test used natural boron only and the small liquid scintillator shows neutron sensitivity (e.g., developing peak at approximately Channel 11).

Thus, as disclosed herein, various exemplary boron compounds of the present disclosure provide transparent mixtures with standard formulations of liquid and cast or extruded plastic scintillators. As shown herein, for example, the mixtures are sensitive to thermal neutron capture on the $^{10}$B introduced by the compounds. Scintillator mixtures may also show pulse shape discrimination for their fast neutron signals.

In addition, advantageously, the boron compounds disclosed herein may be produced using tabletop methods (e.g., using easily available materials worth approximately $55 per liter (for example, tribenzyl borate), and $600 per liter (for example, $^{10}$B enriched tribenzyl borate). Also, with a flashpoint above 100° C., the boron containing compounds are neither flammable nor combustible.

Example 4

Figure 13:
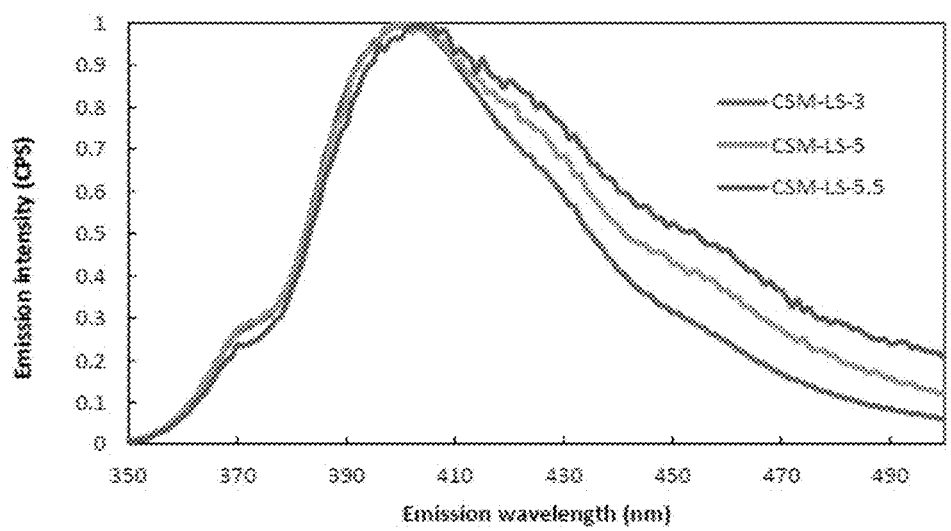
FIG. 13 shows illustrative fluorescence spectra of the compounds of FIG. 1 in accordance with various embodiments of the present disclosure.

The three compounds of FIG. 1 were confirmed as scintillators using a Horiba fluorescence spectrometer, as shown in FIG. 13. FIG. 13 shows fluorescence spectra of the three boron containing liquids without PPO/POPOP addition, and normalized to relative maxima. The spectra were obtained with a Horiba Nanolog. Based on the spectra shown in FIG. 13, fluorescent dopants were added to enhance scintillation. Various liquids having the added fluorescent dopants are shown in FIG. 14 under UV-light.

Figure 14:
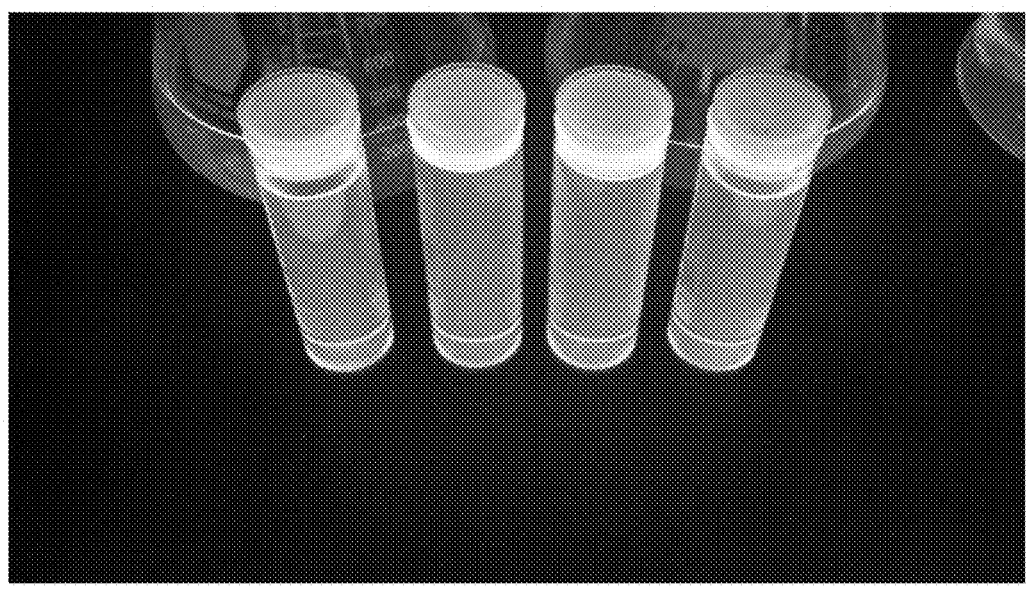
FIG. 14 shows illustrative scintillation results of the compounds of FIG. 1 in accordance with various embodiments of the present disclosure.

FIG. 14 shows scintillation results of the boron compounds. Fluorescent dopants were added to enhance scintillation and tested in a number of combinations. Various liquids that were tested are shown under UV-light in FIG. 14. The three boron compound containing samples are on the right in FIG. 14, and a commercial liquid scintillator (e.g., EJ-301) is on the left in FIG. 14. Advantageous scintillation efficiency was observed with a combination of tribenzyl borate (as well as $^{10}$B enriched tribenzyl borate) with 3% PPO and 0.09% POPOP (alternatively 3% fluorene and 0.09% POPOP). Based on the results shown in FIG. 14, advantageous trends occurred when increasing dopants in the exemplary various liquids.

In addition, apart from the tests with the fluorescence spectrometer, a 137-Cs source (667 keV) was used to test for the response to gamma excitation. The results are shown in FIG. 15.

Figure 15:
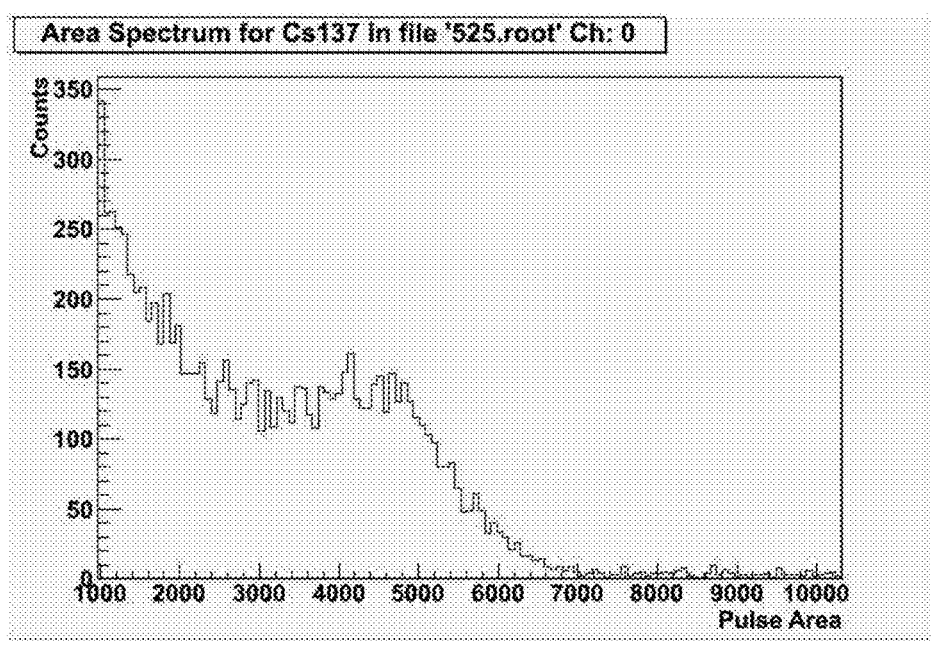
FIG. 15 shows an illustrative a 137Cs test in accordance with various embodiments of the present disclosure.

FIG. 15 clearly shows the Compton edge of the detector response. In particular, FIG. 15 shows a 137-Cs test showing Compton Edge from 667 keV gamma ray in the liquid scintillator $^{10}$B enriched tribenzyl borate.

Figure 16:
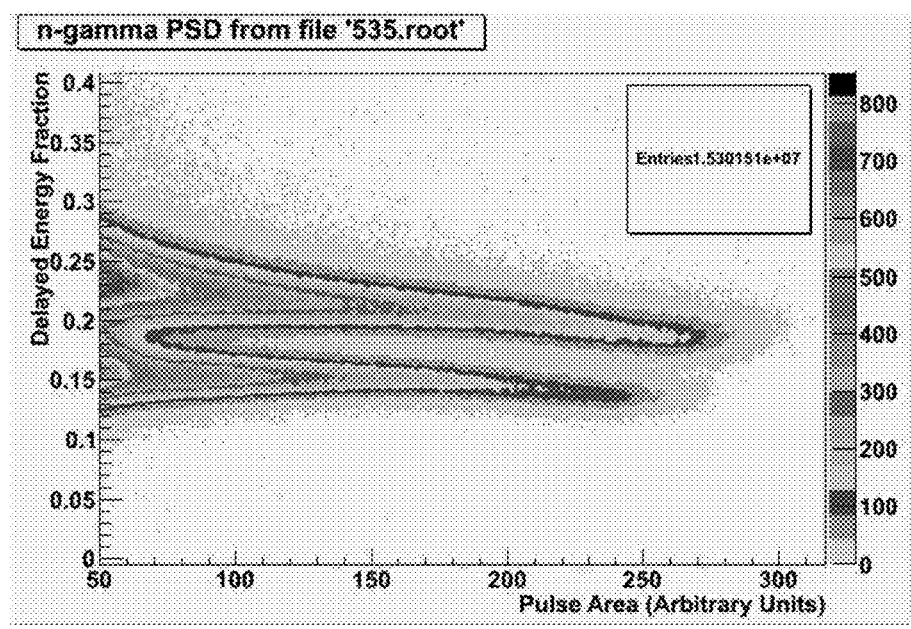
FIG. 16 shows an illustrative spectrum in accordance with various embodiments of the present disclosure.

Further, neutron sensitivity was tested using a 244Cm/13C fast neutron source in two configurations. Initially lead shielding was used to reduce gamma radiation at the scintillator location but let the fast neutron spectrum pass nearly uninhibited. FIG. 16 shows the resulting spectrum.

FIG. 16 shows an illustrative lead shielded 244-Cm/13-C source spectrum of $^{10}$B enriched tribenzyl borate. In various embodiments, FIG. 16 shows that the resulting spectrum (e.g., delayed area versus full pulse area) exhibits neutron-gamma pulse shape discrimination (PSD) and displays the gamma events in the lower horizontal line and the fast neutron events in the upper line. Thus, having PSD together with $^{10}$B capture events advantageously enhances the usefulness of the present scintillators.

In order to establish that the scintillator would be sensitive to the thermal neutron capture on $^{10}$B, which leads to fast alpha particles in the exit channel, the response to energetic alpha particles was also tested by immersing a 241Am source into the scintillator liquids. The results are shown in FIG. 17.

Figure 17:
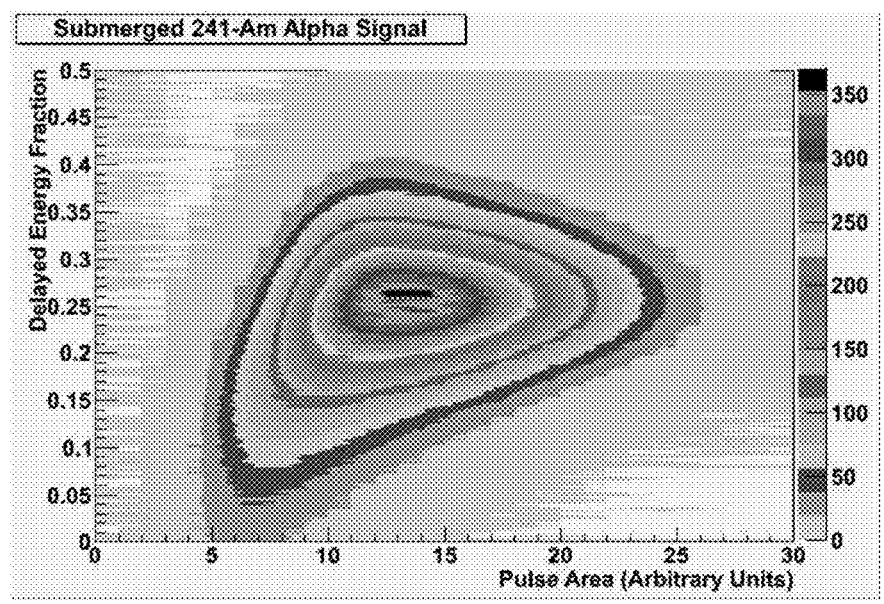
FIG. 17 shows an illustrative 241Am α signal in accordance with various embodiments of the present disclosure.

As can be seen in FIG. 17, the energetic alpha particles leave a clear signal in the $^{10}$B enriched tribenzyl borate sample. In particular, FIG. 17 shows a 241Am α signal in the scintillator $^{10}$B enriched tribenzyl borate.

Figure 18:
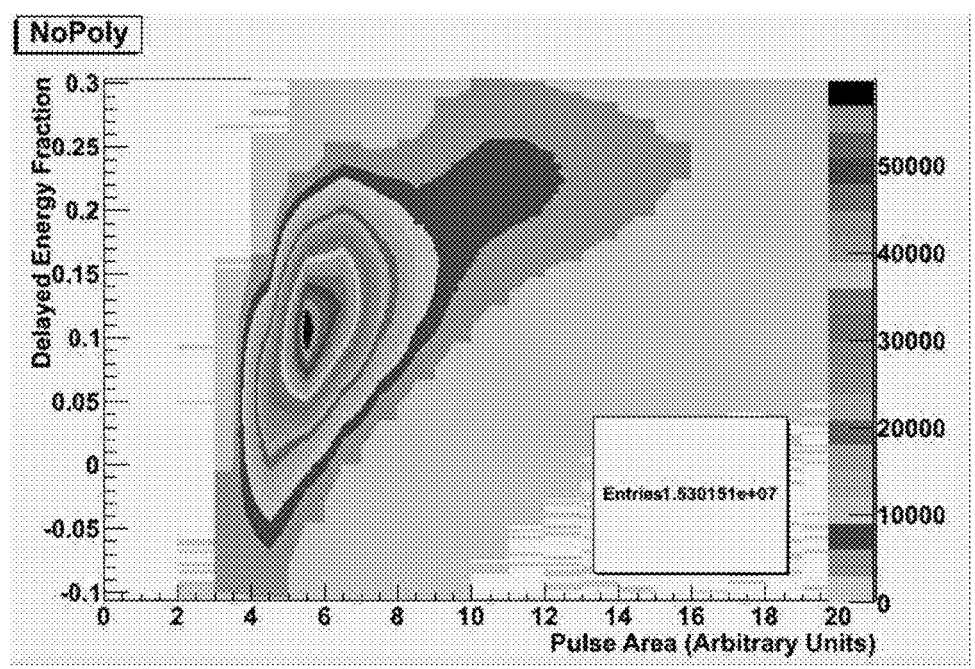
FIG. 18 shows an illustrative 244-Cm/13-C low energy spectrum in accordance with various embodiments of the present disclosure.

Thus, there are indications from the data collected with the fast neutron source that thermal neutron capture in the low energy spectrum may be slightly above the electronic noise at around Pulse area 11 and the delayed area 0.23, as shown in FIG. 18.

FIG. 18 shows a 244-Cm/13-C low energy spectrum showing electronic noise (PMT, which is also visible when the scintillator was removed) and indications for thermal neutron capture on $^{10}$B. To enhance the thermal neutron flux, a plastic (hydrogen rich) shielding was placed around the scintillator sample. A significant increase in the thermal neutron capture signal on $^{10}$B (together with a decrease in the fast neutron signal was observed (not shown) at the expected location in the low energy spectrum was observed. The increase is shown in FIG. 19.

Figure 19:
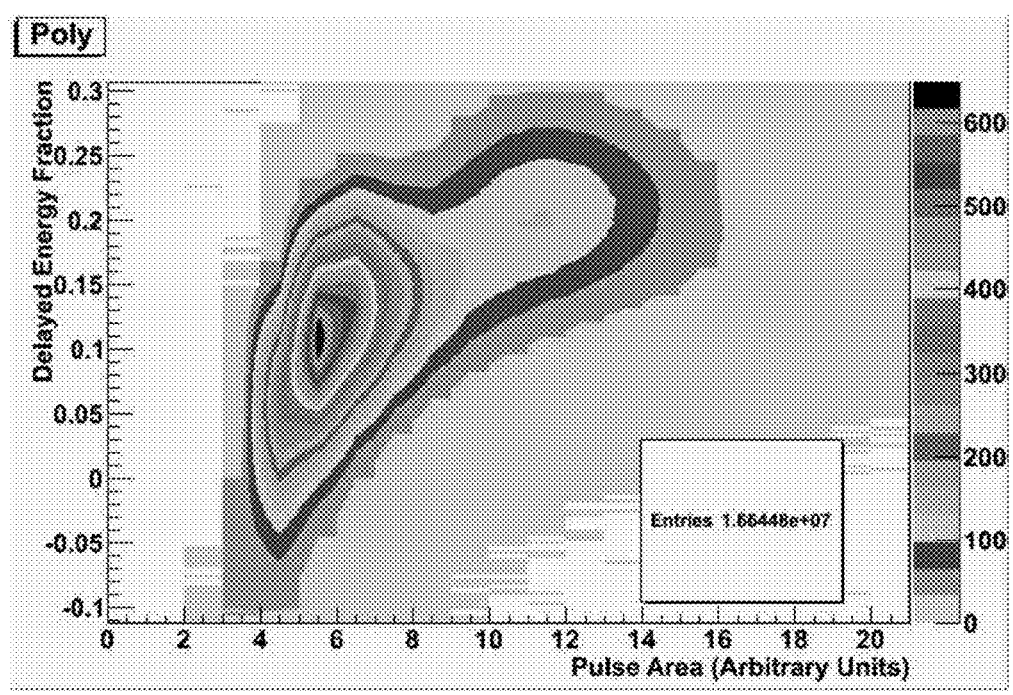
FIG. 19 shows an illustrative thermalized neutron spectrum from a 244-Cm/13-C source in accordance with various embodiments of the present disclosure.

In particular, FIG. 19 shows a thermalized neutron spectrum from a 244-Cm/13-C source in the $^{10}$B enriched tribenzyl borate liquid scintillator.

Thus, the combination of boron compounds with functional groups to produce scintillation may advantageously lead to a liquid scintillator that is neutron sensitive via neutron-proton scattering, and neutron capture on $^{10}$B. The scintillator also advantageously may exhibit gamma-neutron pulse shape discrimination, which is important for the identification of fast neutrons. Also, the scintillator can advantageously be produced with tabletop methods using easily available materials (e.g., worth approximately $55/liter (for tribenzyl borate) and $600/liter (for $^{10}$B enriched tribenzyl borate)). In addition, with flashpoints above 150° C., the scintillators are advantageously neither flammable nor combustible.

Figure 20:
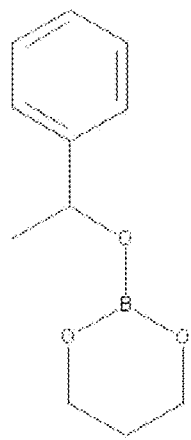
FIG. 20 shows an illustrative molecular structure of CPA 51 in accordance with various embodiments of the present disclosure.

In various embodiments, an illustrative extrusion process may include drying polycarbonate overnight under vacuum at a temperature of 140° C. and mixing 2 grams of PPO and 0.04 g of POPOP dissolved in 40 g of warm CPA51 (CPA51 is 2-alpha-methylbenzyloxy-1,3,2-dioxaborinan). CPA51 is a borate ester obtained using methods disclosed herein, and using one unit of alpha-methylbenzyl alcohol and one unit of propanediol for every unit of boric acid. CPA51 is advantageously more soluble in polycarbonate than the other exemplary borate esters. FIG. 20 shows an illustrative molecular structure of CPA 51. The CPA51 mixture was mixed with 158 g of the dried polycarbonate and fed to a single-screw extruder. The temperature setpoints of the extruder barrels were T1=240° C., T2=220° C., and T3=220° C., where the temperatures are measured at even distances down the length of the barrel and T1 was the temperature closest to the feeder. The screw speed was set at 20 rpm. The resulting hot extrudate was shaped into disks.

In further embodiments, additional illustrative samples were tested. The samples contained 20 weight (wt.) % of CPA51, 1 wt. % of PPO and 0.02 wt. % of POPOP in a polycarbonate matrix. The mixture was extruded at temperatures between 220° C. and 240° C. in a single-screw extruder.

In still further embodiments, additional illustrative boron-loaded polycarbonate samples scintillated and reached about 40% of the efficiency of a commercial sample of Eljen plastic scintillator EJ-204. The boron-loaded polycarbonate samples had a Glass Transition Temperature (Tg) around about 80° C., which is improved over polystyrene samples with the same amount of boron, which had a Tg around 40° C.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. The features of the embodiments of the disclosure may be combined in alternate embodiments other than those discussed above.

Moreover, though the description of the disclosure has included description of one or more embodiments and certain variations and modifications, other variations, combinations, and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A compound for use in scintillation, comprising:
a boron compound, wherein the boron compound is liquid borate ester and wherein the borate ester compound is soluble,
wherein the boron compound is a borate ester synthesized according to $B(OH)_3 + 3ROH = B(OR)_3 + 3 H_2O$, and R comprises at least one of ethanol, methanol, propanol, butanol, benzyl alcohol, phenol, pyrocatechol, ethylene glycol, and propylene glycol, and wherein the compound further comprises at least one of 2,5 diphenyloxazole, 1,4,4-tetraphenyl-1,3-butadiene, p-terphenyl, p-quaterphenyl, 1,4-diphenyl-1,3-butadiene, stilbene, biphenyl, 1,6-diphenyl-1,3,5-hexatriene, diphenylacetylene, diphenyldiacetylene, 2,4-bis(5-phenyloxazole-2-yl)benzene, 9,10-diphenylanthracene, 1,3-diphenyl-2-pyrazoline, diphenylethane, and 1-phenyl-1,3,3-trimethylindan.

2. The compound of claim 1, wherein the boron compound comprises a functionalized boron.

3. The compound of claim 1, wherein the boron compound is $B(OR)_3$.

4. The compound of claim 1, wherein the compound is admixed to a scintillator compound.

5. The compound of claim 4, wherein the scintillator compound is used in a plastic scintillator.

6. The compound of claim 4, wherein the scintillator compound is used in a liquid scintillator.

7. The compound of claim 1, wherein the borate ester further comprises a functional group of at least one of benzyl alcohol, propylene glycol, ethylene glycol, ethanol, methanol, propanol, butanol, phenol, and pyrocatechol.

8. The compound of claim 1, further comprising at least one of anthracene and naphthalene.

9. A method of detecting scintillation, comprising:
monitoring a detection device, wherein the detection device comprises a borate ester compound, wherein the borate ester compound is soluble, and wherein the boron ester compound is a borate ester synthesized according to $B(OH)_3 + 3ROH = B(OR)_3 + 3 H_2O$, and R comprises at least one of ethanol, methanol, propanol, butanol, benzyl alcohol, phenol, pyrocatechol, ethylene glycol, and propylene glycol, and wherein the compound further comprises at least one of 2,5 diphenyloxazole, 1,4,4-tetraphenyl-1,3-butadiene, p-terphenyl, p-quaterphenyl, 1,4-diphenyl-1,3-butadiene, stilbene, biphenyl, 1,6-diphenyl-1,3,5-hexatriene, diphenylacetylene, diphenyldiacetylene, 2,4-bis(5-phenyloxazole-2-yl)benzene, 9,10-diphenylanthracene, 1,3-diphenyl-2-pyrazoline, diphenylethane, and 1-phenyl-1,3,3-trimethylindan; and
detecting scintillation.

10. The method of claim 9, wherein the detection device further comprises a fluorescent dopant.

11. The method of claim 9, wherein the borate ester compound is a non-flammable borate ester compound.

12. The method of claim 10, wherein the fluorescent dopant and the borate ester compound are combined using continuous extrusion.

13. A scintillation device, comprising:
a borate ester compound, wherein the borate ester compound is soluble, and wherein the boron ester compound is a borate ester synthesized according to $B(OH)_3 + 3ROH = B(OR)_3 + 3 H_2O$, and R comprises at least one of ethanol, methanol, propanol, butanol, benzyl alcohol, phenol, pyrocatechol, ethylene glycol, and propylene glycol, and wherein the compound further comprises at least one of 2,5 diphenyloxazole, 1,4,4-tetraphenyl-1,3-butadiene, p-terphenyl, p-quaterphenyl, 1,4-diphenyl-1,3-butadiene, stilbene, biphenyl, 1,6-diphenyl-1,3,5-hexatriene, diphenylacetylene, diphenyldiacetylene, 2,4-bis(5-phenyloxazole-2-yl)benzene, 9,10-diphenylanthracene, 1,3-diphenyl-2-pyrazoline, diphenylethane, and 1-phenyl-1,3,3-trimethylindan.

14. The device of claim 13, wherein the borate ester compound is a standalone scintillator and a product of commercially available 10-B boric acid.

15. The device of claim 14, wherein the borate ester compound is a non-flammable borate ester compound that is soluble as an additive in a liquid scintillator solution.

16. The device of claim 13, wherein the detection device further comprises an electronic light sensor.

17. The device of claim 13, wherein the device uses a pulse shape discriminator in the scintillation.

* * * * *

UNITED STATES PATENT AND TRADEMARK OFFICE
CERTIFICATE OF CORRECTION

| | | |
|---|---|---|
| PATENT NO. | : 9,796,921 B2 | Page 1 of 1 |
| APPLICATION NO. | : 14/452007 | |
| DATED | : October 24, 2017 | |
| INVENTOR(S) | : Cory Pecinovsky et al. | |

It is certified that error appears in the above-identified patent and that said Letters Patent is hereby corrected as shown below:

In the Specification

Column 1, Line 13:
Insert:
--GOVERNMENT LICENSE RIGHTS
This invention was made with government support under HDTRA1-11-1-0025 awarded by the Department of Energy. The government has certain rights in the invention.--

Signed and Sealed this
Eleventh Day of September, 2018

Andrei Iancu
*Director of the United States Patent and Trademark Office*